United States Patent [19]

Ager, Jr.

[11] Patent Number: 4,997,970

[45] Date of Patent: Mar. 5, 1991

[54] CONVERSION OF PYRETHROID ISOMERS TO MOVE ACTIVE SPECIES

[75] Inventor: John W. Ager, Jr., Princeton, N.J.

[73] Assignee: FMC Corporation, Philadelphia, Pa.

[21] Appl. No.: 197,725

[22] Filed: May 23, 1988

Related U.S. Application Data

[63] Continuation-in-part of Ser. No. 62,274, Jun. 15, 1987, abandoned.

[51] Int. Cl.$^5$ .................. C07C 253/32; C07C 253/34; C07C 255/31; C07C 255/39
[52] U.S. Cl. .................................... 558/354; 558/355; 558/407; 560/124
[58] Field of Search ....................... 558/354, 355, 407; 560/124

[56] References Cited

U.S. PATENT DOCUMENTS

| | | |
|---|---|---|
| 4,213,916 | 7/1980 | Davies et al. ......................... 558/354 |
| 4,287,208 | 9/1981 | Fuchs et al. ......................... 558/354 |
| 4,308,279 | 12/1981 | Smeltz ............................. 558/354 X |
| 4,427,598 | 1/1984 | Mason et al. ......................... 558/354 |
| 4,512,931 | 4/1985 | Robson .............................. 558/354 |
| 4,544,508 | 10/1985 | Fuchs et al. ......................... 558/354 |
| 4,544,510 | 10/1985 | van Berkel et al. ................. 558/354 |
| 4,656,303 | 4/1987 | Kurono et al. ....................... 558/354 |
| 4,670,464 | 6/1987 | Doyle et al. ......................... 514/521 |
| 4,681,969 | 7/1987 | Williams et al. ..................... 558/407 |
| 4,733,001 | 3/1988 | Suzuki et al. ........................ 558/354 |
| 4,782,174 | 11/1988 | Fuchs et al. ......................... 558/354 |
| 4,845,126 | 7/1989 | Hidasi et al. ......................... 514/521 |

FOREIGN PATENT DOCUMENTS

86/04215 7/1986 PCT Int'l Appl. .
86/04216 7/1986 PCT Int'l Appl. .
2064528A 6/1981 United Kingdom .

OTHER PUBLICATIONS

Merch Index, 10th Edition, Compound 7050, p. 1033 (1983).
Aldrich Catalog Handbook of Fine Chemicals (1986), p. 39.

Primary Examiner—Joseph Paul Brust
Attorney, Agent, or Firm—H. Robinson Ertelt; Patrick C. Baker

[57] ABSTRACT

Crystallizable pyrethroid isomers or enantiomer pairs are converted to more pesticidally active isomers by contacting a hydrocarbon slurry of the starting isomers with a base and a catalyst, the catalyst being substantially soluble in the slurry and selected from a quaternary ammonium compound, a quaternary phosphonium compound and a crown ether, agitating the slurry while maintaining a temperature effective for conversion, and recovering the resulting isomers. The tendency to form benzoin ester by-product is reduced by including in the slurry a weak base, an aldehyde scavenger such as a metabisulfite, and/or a tetraalkyl ($C_1$-$C_5$) ammonium halide catalyst dissolved in an aprotic solvent such as an organic nitrile. The process typically is effective for enriching cypermethrin, cyfluthrin and (cyano (3-phenoxyphenyl)methyl 3-(2,2-dibromoethenyl)-2,2-dimethylcyclopropanecarboxylate in the more active species.

31 Claims, No Drawings

CONVERSION OF PYRETHROID ISOMERS TO MOVE ACTIVE SPECIES

RELATED APPLICATION

This application is a continuation-in-part of application Ser. No. 62,274 filed June 15, 1987, and abandoned as of the filing of this application.

TECHNICAL FIELD

This invention relates to the transformation of pyrethroid isomers into isomers which are more pesticidally active than the starting isomers.

BACKGROUND OF THE INVENTION

The pyrethroids with which the present invention is concerned are crystallizable esters having at least one asymmetric carbon atom to which an epimerizable proton is attached. The more pesticidally active pyrethroids additionally contain at least one and usually two or more other asymmetric carbon atoms and therefore comprise isomeric mixtures wherein one or more of the isomers are more pesticidally active than the others. Representative of such pyrethroids are the alpha-cyanobenzyl esters of the formula (A):

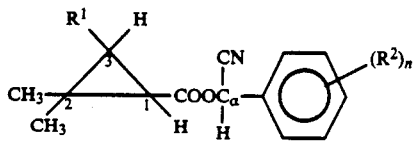

wherein $R^1$ is halogen, haloalkyl, alkenyl or haloalkenyl; each $R^2$ independently is halogen, alkyl, haloalkyl, alkoxy, phenyl, phenoxy, phenylalkyl, substituted phenyl and substituted phenylalkyl wherein the substituents include one or more of alkyl, halogen, haloalkyl, nitro, hydroxy and cyano; and n is 0–5, preferably 1–3.

In the above formula the asymmetric carbon atoms are marked 1, 3 and alpha. All of the substituents on a host group may be the same, or the substituents may be different. Alkyl and alkoxy may contain 1–8 carbon atoms, preferably 1–4 carbon atoms. Alkenyl may comprise 2–8 carbon atoms, preferably 2–4 carbon atoms. Halogen includes fluorine, chlorine and bromine. A typical phenylalkyl group is benzyl. Substituted phenyl includes tolyl, xylyl, trichlorophenyl and trifluoromethylphenyl. Substituted phenylalkyl includes methylbenzyl, trichlorobenzyl and trifluoromethylbenzyl.

The foregoing and other pyrethroids are well known as disclosed, for example, in Kirk-Othmer, Encyclopedia of Chemical Technology, Second Edition, Vol. 13, pages 456–458, in the following U.S. Patents:

U.S. Pat. No. 4,024,163—Elliot et al (NRDC)
U.S. Pat. No. 4,133,826—Warnant et al (Roussel Uclaf)
U.S. Pat. No. 4,136,195—Warnant et al (Roussel Uclaf)
U.S. Pat. No. 4,213,916—Davies et al (Shell)
U.S. Pat. No. 4,287,208—Fuchs et al (Bayer)
U.S. Pat. No. 4,308,279—Smeltz (FMC)
U.S. Pat. No. 4,427,598—Mason et al (Shell)
U.S. Pat. No. 4,512,931—Robson (ICI)
U.S. Pat. No. 4,544,508—Fuchs et al (Bayer)
U.S. Pat. No. 4,544,510—Van Berkel et al (Shell)
U.S. Pat. No. 4,560,515—Stoutamire et al (Shell)
U.S. Pat. No. 4,582,646—Stoutamire et al (Shell)
U.S. Pat. No. 4,670,464—Doyle et al (ICI)
U.S. Pat. No. 4,681,969—Williams et al (ICI)

and in the following PCT patent publications:

WO 86/04215 - Hidasi et al (Chinoin)
WO 86/04216 - Hidasi et al (Chinoin)

All of the listed patents and publications are incorporated herein by reference.

Preferred pyrethroids convertible to more active isomers in accordance with the present invention are those of formula A wherein $R^1$ is dihalovinyl or tetrahalopropenyl, $R^2$ is phenoxy, and n is 1. The more preferred pyrethroids are those wherein n is 1, $R^1$ is dihalovinyl or tetrahalopropenyl and $R^2$ is phenoxy; and those wherein n is 2, $R^1$ is dihalovinyl or tetrahalopropenyl and one $R^2$ is fluorine and the other $R^2$ is phenoxy. The latter preferred compounds are isomeric mixtures having the common name "cyfluthrin" when $R^1$ is dichlorovinyl, n is 2 and one $R^2$ is fluorine. When $R^1$ is dichlorovinyl, n is 1 and $R^2$ is phenoxy, the mixtures have the common name "cypermethrin."

Cypermethrin contains four cis and four trans isomers designated I-VIII as follows:

| | cis isomers |
|---|---|
| I. | (S)(α-cyano)(3-phenoxyphenyl)methyl 1R,cis-3-(2,2-dichloroethenyl)-2,2-dimethylcyclopropanecarboxylate (abbreviated 1R,cis S) |
| II. | (R)(α-cyano)(3-phenoxyphenyl)methyl 1S,cis-3-(2,2-dichloroethyl)-2,2-dimethylcyclopropanecarboxylate (abbreviated 1S,cis R) |
| III. | (S)(α-cyano)(3-phenoxyphenyl)methyl 1S,cis-3-(2,2-dichloroethenyl)-2,2-dimethylcyclopropanecarboxylate (abbreviated 1S,cis S) |
| IV. | (R)(α-cyano)(3-phenoxyphenyl)methyl 1R,cis-3-(2,2-dichloroethenyl)-2,2-dimethylcyclopropanecarboxylate (abbreviated 1R,cis R) |
| | trans isomers |
| V. | The trans isomer of I (abbreviated 1R,trans S) |
| VI. | The trans isomer of II (abbreviated 1S,trans R) |
| VII. | The trans isomer of III (abbreviated 1S,trans S) |
| VIII. | The trans isomer of IV (abbreviated 1R,trans R) |

Cyfluthrin and other pyrethroids to which the invention is applicable comprise similar isomeric mixtures.

It is known that the most insecticidally active isomers of the foregoing eight isomers are I and V, and that enantiomer pairs I/II (abbreviated cis-2) and V/VI (abbreviated trans-2) are more insecticidally active than the enantiomer pairs III/IV (abbreviated cis-1) and VII/VIII (abbreviated trans-1). It is extremely difficult and commercially impractical to separate the more active isomers such as I and V from the complex isomer mixtures produced in the usual pyrethroid synthesis. Accordingly, efforts to produce more pesticidally active pyrethroids have focused on techniques for converting less active isomers in the synthesis product mixtures to more active isomers, i.e., to enrich isomeric mixtures with respect to the more active isomers, thus avoiding complex resolution procedures and the loss represented by discard of less active isomers.

Nevertheless, even when the isomeric mixtures have been converted rather than resolved, the conversion procedures have not been commercially practical because of poor yields, usually due to production of undesired by-product, often comprising as many isomers as the desired product, and because of time-consuming multiple steps, high temperatures and/or the need to recover expensive reagents. In the case of cypermethrin the major by-product is (R,S)-2-oxo-1,2-bis(3-phenoxyphenyl) ethyl cis- and trans-3-(2,2-dichloroethenyl)-2,2-dimethylcyclopropanecarboxylate, an eight isomer mixture commonly called the "benzoin by-product." Similar by-products are encountered in the synthesis of other pyrethroids such as cyfluthrin. Representative of prior efforts to convert isomer mixtures to more active species are the procedures disclosed in U.S. Pat. Nos. 4,213,916, 4,308,279, 4,544,510, 4,544,508, 4,512,931, 4,427,598, 4,670,646 and 4,681,969 and the two PCT patent publications cited above.

SUMMARY OF THE INVENTION

It has now been found, in accordance with one aspect of the invention, that crystallizable pyrethroid isomers can be converted to the desired, more pesticidally active, isomers by contacting a hydrocarbon solvent slurry of a starting mixture of the isomers with a base and a catalyst, agitating the resulting mixture at a temperature effective for conversion, and recovering the resulting crystallized, more active isomers.

In another aspect of the invention, single less active isomers are converted by the treatment to single more active isomers, or less active diastereomer mixtures are converted to single more active isomers, or a starting mixture of more active and less active enantiomer pairs is converted to an enantiomer pair mixture enriched, i.e., predominating, in the more active enantiomer pairs.

In still other aspects of the invention the starting isomeric mixture is a mixture of all of the enantiomer pairs of cypermethrin or cyfluthrin, single pairs thereof, or any combination of the pairs such as the cis-1 and cis-2 pairs and the trans-1 and trans-2 pairs, and the product mixture contains higher proportions of the more active enantiomer pairs.

By the process of the invention pesticidally inactive or less active isomers or enantiomers are converted to active or more active isomers or enantiomers, and mixtures of both the more active and less active isomers or enantiomers are enriched in the more active isomers or enantiomers. The process is effective at room temperature range and with solvents which are usable in the preceding esterification reaction in which the pyrethroids are formed, thus presenting opportunity for avoiding solvent exchange. Moreover, the reagents for the conversion are inexpensive and by-product is substantially reduced with concomitant increased yield of more active product. The process therefore is eminently suitable for commercial production.

By-product is effectively reduced by employing as the base a weakly basic compound such as an alkali metal salt of a weak acid, and is more effectively reduced by adding an aldehyde scavenger to the reaction slurry containing the base. The aldehyde scavenger is believed to suppress the formation of benzoin ester by-product by reacting with aldehydes believed to be present as intermediates to the benzoin esters.

DETAILED DESCRIPTION

While the following description emphasizes application of the invention to isomers of cypermethrin and cyfluthrin, it will be understood that the invention is applicable to any crystallizable pyrethroid isomer or isomeric mixture, that is, to crystallizable pyrethroid compounds having at least one asymmetric carbon atom carrying an epimerizable proton. However, the invention is especially adapted to treatment of crystallizable pyrethroids having an epimerizable proton on an asymmetric carbon atom and a plurality of asymmetric carbon atoms. Such pyrethroids normally comprise mixtures of numerous isomers including enantiomer pairs, such as the eight isomers (four enantiomer pairs) of cypermethrin and cyfluthrin, described above. As pointed out above, the more isomers a pyrethroid comprises, the more difficult and expensive it is to produce the more active isomers or mixtures enriched therein. In this specification, "isomers" means and includes enantiomer pairs as well as individual isomers and isomer mixtures.

Accordingly, the starting material of the invention may be either a crude material, such as an unpurified reaction mixture containing crystallizable pyrethroid isomers, or the starting material may be purified so that it contains known isomers and proportions thereof. While the starting material initially may be in the liquid state it is necessary for the success of the invention that crystallization be initiated in a liquid medium so that the material is in a slurry form when contacted and agitated with the base and catalyst. Thus the starting material may either be totally solid or may be a liquid mixture in which crystallization is induced by seeding with one or more crystals of the more active isomers it is desired to produce. Preferably, the starting material is totally solid.

The liquid medium in which the slurry is formed consists essentially of an inert, nonpolar, hydrocarbon solvent in which the desired isomers are substantially insoluble. Such inert hydrocarbons include aliphatic or cycloaliphatic hydrocarbons which are liquids in an ambient temperature range for plant processes, e.g., about 5°-35° C., preferably 10°-25° C. Generally, the hydrocarbons contain about 5-16 carbon atoms, preferably 6-8 carbon atoms, and therefore include straight chain and branched pentanes, hexanes, heptanes, octanes, the cyclic counterparts thereof, and any mixtures thereof.

Other solvents may be used with the hydrocarbons in the liquid medium provided they are not present in such amounts as will reduce or destroy the effectiveness of the treatment. For example, while some water or a polar organic liquid such as acetonitrile may be present in the liquid medium, it has been determined that polar liquids tend to inhibit the process by rendering the pyrethroids more soluble and thus reduce the yields of the desired more active isomers Water in major amounts is also undesirable because it decreases yield by increasing by-product. Likewise, the hydrocarbon solvent may include minor amounts of aromatic hydrocarbon components; again such components reduce the yield of useful product, principally by increasing solubility, thereby inhibiting crystallization. The liquid medium of the slurry therefore must predominately comprise an inert hydrocarbon solvent selected for substantial insolubility of the desired isomers therein.

The solvent is used in an amount which provides a fluid medium for the conversion process and such that the medium can be agitated easily. About 1-10 parts by weight of solvent per part by weight of pyrethroid starting material usually will be sufficient but the amount may be varied depending upon the starting material. A preferred proportion is about 2-4 parts by weight of solvent per part by weight of pyrethroid.

Bases used in the process may include both strong and weak inorganic bases of which the following are representative: alkali or alkaline earth metal oxides, hydroxides, carbonates, bicarbonates, cyanides, cyanates, acetates and borates, and alkali metal fluorides such as KF. Other bases include organic amino compounds such as trialkylamine wherein the alkyl group contains 1 to about 8 carbon atoms, including both straight and branched alkyl groups, such as triethylamine, and N-heterocycles such as pyridine, quinoline, pyrrole, pyrazole, pyrrolidine, and the like. Preferably the bases are basic salts of organic or inorganic acids such as sodium or potassium carbonate, bicarbonate, acetate and cyanide, and the potassium salt of 3-(2,2-dichloroethenyl)ethenyl)-2,2-dimethylcyclopropanecarboxylic acid. The bases may be used singly or in any mixtures of two or more thereof.

The bases preferably are added to the hydrocarbon solvent medium as solids. Aqueous solutions of one or more of the foregoing bases may be used but the amount of water contributed by the solution to the liquid medium must not be such as to impede the process or reduce the yield of crystalline product, as mentioned above. The amount of base may be varied depending on its strength and the economics of the treatment, e.g., residence time of the process. Weaker bases may require longer treatment time than stronger bases, and smaller amounts of stronger bases may permit treatment times equivalent to those required when weaker bases are used. Typically, for a base having a $pK_a$ of about 9-11, about 1 part by weight of base per 10 parts by weight of pyrethroid starting material will be effective and for a base having a $pK_a$ over 11, less than 1 part by weight of base per 10 parts by weight of pyrethroid will be sufficient.

To further reduce benzoin by-products it is preferred to add an aldehyde scavenger to the reaction slurry, either directly or indirectly by admixture with the base, to react with aldehydes which are believed to be present as intermediates to undesired benzoin ester by-products. Suitable aldehyde scavengers include alkali metal metabisulfites, hydrogen sulfites and hydrosulfites such as sodium metabisulfite, sodium hydrosulfite and sodium hydrogen sulfite. The aldehyde scavengers are employed in weight ratios relative to base of from about 2:1 to 1:2, preferably about 1:1. Preferred base/aldehyde scavenger pairs for optimizing suppression of benzoin by-products are potassium cyanide/sodium metabisulfite, sodium cyanide/sodium hydrogen sulfite, sodium cyanide/sodium hydrosulfite and potassium cyanide/potassium metabisulfite.

Useful catalysts include quaternary ammonium or phosphonium compounds and crown ethers different from the base. Suitable quaternary compounds are commercially available and include the following, either singly or in any admixture: Methyl($C_8$–$C_{10}$-trialkyl)ammonium chloride
Benzyltributylammonium chloride
Benzyltriethylammonium chloride
Benzyltrimethylammonium chloride
Benzyltriphenylphosphonium chloride
n-Butyltriphenylphosphonium bromide
Cetyltrimethylammonium bromide
Dodecyltriphenylphosphonium bromide
Ethyltriphenylphosphonium bromide
Methyltributylammonium iodide
Methyltriphenylphosphonium bromide
Myristyltrimethylammonium bromide
Phenyltrimethylammonium bromide
Phenyltrimethylammonium tribromide
n-Propyltriphenylphosphonium bromide
Tetrabutylammonium bromide
Tetrabutylammonium chloride
Tetrabutylammonium hydrogen sulfate
Tetrabutylammonium hydroxide
Tetraethylammonium bromide
Tetramethylammonium chloride
Tetramethylammonium fluoride pentahydrate
Tetramethylammonium hexafluorophosphate
Tetramethylammonium hydroxide
Tetramethylammonium tetrafluoroborate
Tetraethylammonium chloride
Tricaprylmethylammonium chloride
Tris(3,6-dioxaheptyl)amine.

Other halides in addition to those listed may be used, such as the bromides, chlorides, and some iodides. The catalyst may also be reacted with a base to form a compound suitable for the treatment. Typical of such compounds are tricaprylmethylammonium phenolate, tricaprylmethylammonium methylate, benzyltrimethylammonium hydroxide, benzyltrimethylammonium methoxide, tetraethylammonium hydroxide, and tetrabutylammonium cyanide.

Since the shorter chain ($C_1$–$C_5$) quaternary catalysts are less soluble in the hydrocarbon solvent of the process than are the longer chain quaternaries, it is desirable to dissolve the shorter chain quaternary catalyst in an aprotic organic solvent such as an organic nitrile (acetonitrile, propionitrile, or the like) prior to addition of the catalyst to the reaction medium. The amount of aprotic solvent will be about equivalent to the weight of catalyst. Too much of the solvent may dissolve the starting pyrethroid isomers and thereby prevent formation of the reaction slurry necessary for the desired high conversion to more active isomers.

The crown ethers include 18-crown-6 and other variations thereof such as benzo-15-crown-5, 12-crown-4, 15-crown-5, dibenzo-18-crown-6, dibenzo-24-crown-8, dicyclohexano-18-crown-6, and the like. The foregoing and other crown ethers are commercially available and are reviewed in the literature such as Gokel and Durst, "Crown Ether Chemistry: Principles and Applications", Aldrichimica Acta, 9(1), 3–12(1976), incorporated herein by reference.

The crown ethers and shorter chain quaternaries (including the basic adducts thereof) tend to lose their effectiveness in aqueous media. Therefore, these catalysts are preferably used when the hydrocarbon solvent liquid medium is anhydrous. The preferred catalysts are tricaprylmethylammonium chloride, tetrabutylammonium chloride or tetraethylammonium chloride in acetonitrile, tris(3,6-dioxa-heptyl)amine, and 18-crown-6. The preferred liquid medium is anhydrous heptane. The preferred base is sodium cyanide.

Suitable amounts of catalyst are about 0.1–1.0 parts by weight of catalyst per 10 parts by weight of pyrethroid starting material, preferably about 0.2–0.5 parts by weight of catalyst per 10 parts by weight of pyrethroid. The catalyst may be added to the pyrethroid slurry in a single addition or incrementally, such as about half initially and the balance over several hours, e.g., 3–8 hours later.

Sequence of addition of the reagents to the liquid medium normally is not critical; any of the reagents including the pyrethroid starting material may be present initially or added later. Moreover, base and catalyst may be added as a preformed adduct or the components may be added separately. In the case of a base-catalyst adduct, sequential addition is preferred, such as about half initially and the second half about 3–8 hours later. The sequence of addition, amounts and proportions of reagents, however, may be adjusted to minimize the production of undesirable by-product such as benzoin esters. The preferred sequence of addition is to stir the pyrethroid starting material with the aldehyde scavenger in the solvent for about two hours and then add the base and catalyst to the mixture.

The slurry containing pyrethroid isomers, base and catalyst is agitated for such time and at such temperature as to induce conversion to the desired isomers. One of the advantages of the invention is that the conversion may be carried out at conventional ambient temperature conditions such as about 5°-35° C., preferably about 10°-25° C. Typically, the reaction mixture is agitated for about 2 to about 10 hours, preferably about 3 to 8 hours, whereupon the crystalline products may be recovered by any conventional means, such as filtration, evaporation, decantation, centrifugation or any combination thereof. Although the reaction mixture can be cooled prior to filtration, it is preferred that the temperature be maintained throughout the process to reduce the possibility of trapping undesired impurities in the crystalline structure of the product. If desired, the product may be recrystallized one or more times to upgrade purity.

The hydrocarbon solvent is believed to be critical to the success of the process because it has been found that the more active isomers are less soluble therein than are the less active isomers, as compared with the solubilities in a base alone, such as triethylamine, or other solvent. At equilibrium, therefore, formation of the more active isomers is favored and is further promoted by removal of the solid, more active species as it is formed. Accordingly, by using a hydrocarbon as the dominant solvent in the process, the reaction is driven to produce the more active cis-2 pair at the expense of the less active cis-1 pair. Similar principles are believed applicable to other isomer mixtures, for example, the conversion of the less active trans-1 pair to the more active trans-2 pair.

By the process of the invention, starting isomeric mixtures containing all four of the enantiomer pairs of cypermethrin or cyfluthrin, e.g., about 15-25 wt. % of the cis-2 pair, and about 15-25 wt. % of the trans-2 pair, the balance to make 100 wt. % being distributed between the cis-1 and trans-1 pairs, can be converted to mixtures predominating in the cis-2 and trans-2 pairs, e.g., at least about 30 wt. % of each pair, preferably to at least about 40 wt. % of each such pair. Moreover, starting mixtures of the cis-1 and cis-2 enantiomer pairs, e.g., about 20-80 wt. % of cis-1 and 80-20 wt. % of cis-2, can be converted to mixtures having increased amounts of the more active cis-2 pair, e.g., 30-90 wt. % or more. Similarly, starting mixtures of the trans-1 and trans-2 enantiomer pairs, e.g., about 20-80 wt. % of trans-1 and 80-20 wt. % of trans-2, are convertible to mixtures having increased amounts of the more active trans-2 pair, e.g., about 30-90 wt. % or more.

The following examples further illustrate the invention. In the examples, the terms cis,trans, cis-1, cis-2, trans-1 and trans-2 refer to the isomers and enantiomer pairs of cypermethrin or cyfluthrin as defined above and as the case may be. In each case the compound name followed by the liquid chromatograph analysis (% area) is further abbreviated as follows: $C_1$=cis-1 enantiomer pair; $C_2$=cis-2 enantiomer pair; $T_1$=trans-1 enantiomer pair; $T_2$=trans-2 enantiomer pair; $B_1$=cis-1 benzoin by-product enantiomer pair; $B_2$=cis-2 benzoin by-product enantiomer pair; $B_3$=trans-1 by-product benzoin enantiomer pair; and $B_4$=trans-2 by-product benzoin enantiomer pair.

EXAMPLE 1

Preparation with Aqueous $Na_2CO_3$ of a Mixture Enriched in the Cis-2 Enantiomer Pair of Cypermethrin To a stirred mixture of 10.0 grams (0.024 mole) of (R,S)-(cyano)(3-phenoxyphenyl)methyl cis-3-(2-2-dichloroethenyl)-2,2-dimethylcyclopropanecarboxylate ($C_1$=53.8, $C_2$=42.0, $T_1$=2.8, and $T_2$=1.2), in 20 g of n-heptane was added 0.1 gram (0.00025 mole) of tricaprylmethylammonium chloride (Aliquat® 336, Aldrich Chemical Co.) and 10 mL of an aqueous, 10% sodium carbonate solution. This mixture was stirred at room temperature for five hours. An additional 0.1 gram of tricaprylmethylammonium chloride was added, and the mixture was stirred at room temperature for 13 hours. The reaction mixture was filtered to yield 8.37 grams of the cis-2 enantiomer pair of (R,S)-(cyano)(3-phenoxyphenyl)methyl cis-3-(2,2-dichloroethenyl)-2,2-dimethylcyclopropanecarboxylate as a solid ($C_1$=4.0, $C_2$=94.0, $B_1$=1.1, $B_2$=0.6).

EXAMPLE 2

Preparation with Solid $Na_2CO_3$ of a Mixture Enriched in the Cis-2 enantiomer pair of cypermethrin A crude reaction mixture solution was assayed by liquid chromatography to contain 30.88 % (R,S)-(cyano)-(3-phenoxyphenyl)methyl cis-3-(2,2-dichloroethenyl)-2,2-dimethylcyclopropanecarboxylate in mixed heptanes. The mixed heptanes solvent was removed from a 32.4 gram sample of the solution to yield 9.96 grams of the cis isomers of cypermethrin, which was assayed by liquid chromatography to contain the following isomers: $C_1$=52.56, $C_2$=41.55, $T_1$=2.6, and $T_2$=2.7. Another 32.4 gram sample of the solution was seeded with cypermethrin crystals having a high cis isomer content (at least 50%) and stirred at room temperature for approximately 18 hours to crystallize. This mixture was treated with 0.1 gram (0.00025 mole) of tricaprylmethylammonium chloride and 0.5 gram of solid sodium carbonate. The mixture was stirred at room temperature for four hours at which time an additional 0.1 gram of tricaprylmethylammonium chloride was added. The reaction slurry was stirred for an additional 3.0 hours at room temperature. The reaction slurry was diluted with 15 mL of an aqueous solution containing 2.0 grams of concentrated hydrochloric acid to neutralize the $Na_2CO_3$ and was stirred for 10 minutes. This mixture was filtered to yield 7.06 grams of the cis-2 enantiomer pair of (R,S)-(cyano)(3-phenoxyphenyl)-methyl cis-3-(2,2-dichloroethenyl)-2,2-dimethylcyclopropanecarboxylate as a solid ($C_1$=4.0, $C_2$=95.0, $T_2$=0.6, $B_2$=0.3).

EXAMPLE 3

Preparation of a Mixture Enriched in the Cis-2 and Trans-2 Enantiomer Pairs of Cypermethrin A stirred mixture of 10.0 grams of n-heptane and 10.0 grams of an aqueous, 10% sodium carbonate solution was cooled to 10° C. Seed crystals of (R,S)-(cyano)(3-phenoxyphenyl)methyl cis-3-(2,2-dichloroethenyl)-2,2-dimethylcyclopropanecarboxylate ($C_1$=54, $C_2$=42, $T_1$=3, $T_2$=1) were added. While continuing to maintain a temperature of 10° C., a solution consisting of 10.0 grams (0.024 mole) of (R,S)-(cyano)(3-phenoxyphenyl)- methyl cis,trans-3-(2,2-dichloroethenyl)-2,2-dimethylcyclopropanecarboxylate ($C_1=26.7$, $C_2=18.9$, $T_1=23.0$, $T_2=15$, and $B_2=0.6$), and 0.2 gram (0.005 mole) of tricaprylmethylammonium chloride in 10.0 grams of n-heptane was added dropwise during a 12 hour period to form a slurry. After complete addition, the slurry was stirred at 10° C. for approximately 18 hours. This mixture was filtered to yield 7.5 grams of the cis-2 and trans-2 enantiomer pairs of (R,S)-(cyano)(3-phenoxyphenyl)methyl cis,trans-3-(2,2-dichloroethenyl)-2,2-dimethylcyclopropanecarboxylate as a solid ($C_1=7$, $C_2=41$, $T_1=7$, $T_2=32$, $B_1=4.6$, $B_2=2.5$ and $B_3=3.8$).

EXAMPLE 4

Preparation of a Mixture Enriched in the Trans-2 Enantiomer Pair of Cypermethrin A slurry of 10.0 grams (0.024 mole) of (R,S)-(cyano)(3-phenoxyphenyl)methyl trans-3-(2,2-dichloroethenyl)-2,2-dimethylcyclopropanecarboxylate ($C_1 + C_2=1.1$, $T_1=55.4$, and $T_2=43.5$), 0.1 gram (0.00025 mole) of tricaprylmethylammonium chloride, and 1.0 gram of sodium carbonate in 20 grams of n-heptane was stirred at room temperature for three hours. An additional 0.1 gram of tricaprylmethylammonium chloride was added, and the mixture was stirred for an additional three hours. The reaction mixture was diluted with 10 mL of water and was stirred for 15 minutes. The resultant mixture was filtered. The filter cake was washed with n-heptane to yield 9.17 gram of the trans-2 enantiomer pair of (R,S)-(3-phenoxyphenyl)methyl trans-3-(2,2-dichloroethenyl)-2,2-dimethylcyclopropanecarboxylate ($T_1=1.7$ and $T_2=97.5$).

EXAMPLE 5

Preparation with Solid $K_2CO_3$ of a Mixture Enriched in the Cis-2 Enantiomer Pair of Cypermethrin A slurry of 10.0 grams (0.024 mole) of solid (R,S)-(cyano)(3-phenoxyphenyl)methyl cis-3-(2,2-dichloroethenyl)-2,2-dimethylcyclopropanecarboxylate ($C_1=51.7$, $C_2=46.8$, and $T_1+T_2=1.5$), 0.25 gram (0.00095 mole) of 18-crown-6, and 1.0 gram (0.0072 mole) of potassium carbonate in 20.0 grams of n-heptane was stirred at room temperature for approximately 18 hours. Dilute hydrochloric acid was added to the reaction mixture to neutralize the potassium carbonate. This mixture was stirred at room temperature for two days. The mixture was filtered, and the filter cake was dried to yield 8.72 grams of the cis-2 enantiomer pair of (R,S)-(cyano)(3-phenoxyphenyl)methyl cis-3-(2,2-dichloroethenyl)-2,2-dimethylcyclopropanecarboxylate ($C_1=3.8$, and $C_2=94.9$).

EXAMPLE 6

Preparation of a Mixture Enriched in the Cis-2 Enantiomer Pair of Cyfluthrin A slurry of 5.0 grams (0.012 mole) of solid (R,S)-(cyano)(4-fluoro-3-phenoxyphenyl)methyl cis-3-(2,2-dichloroethenyl)-2,2-dimethylcyclopropanecarboxylate ($C_1=49.2$ and $C_2=50.8$), 0.5 gram (0.0047 mole) of sodium carbonate, and 0.05 gram (0.00012 mole) of tricaprylmethylammonium chloride in 10.0 grams of n-heptane was stirred at room temperature for four hours. An additional 0.05 gram of tricaprylmethylammonium chloride was added, and the slurry was stirred at room temperature for approximately 13 hours. The basic reaction mixture was neutralized with dilute hydrochloric acid and was stirred for approximately 30 minutes. This mixture was filtered, and the filter cake was dried to yield 4.45 grams of the cis-2 enantiomer pair of (R,S)-(cyano)(4-fluoro-3-phenoxyphenyl)methyl cis-3-(2,2-dichloroethenyl)-2,2-dimethylcyclopropanecarboxylate ($C_1=0.1$ and $C_2=99.8$).

EXAMPLE 7

Preparation with Triethylamine of a Mixture Enriched in the Cis-2 Enantiomer Pair of Cypermethrin A slurry of 10.0 grams (0.024 mole) of (R,S)-(cyano)(3-phenoxyphenyl)methyl cis-3-(2,2-dichloroethenyl)-2,2-dimethylcyclopropanecarboxylate ($C_1=53.8$, $C_2=42.0$, $T_1=2.8$, $T_2=1.2$), 0.1 gram (0.00025 mole) of tricaprylmethylammonium chloride, and 8.0 grams (0.079 mole) of triethylamine in 20 grams of n-heptane was stirred at room temperature for 5.5 hours. An additional 0.1 gram of tricaprylmethylammonium chloride was added, and the mixture was stirred for an additional 17 hours. The slurry was filtered and the filter cake was washed with n-heptane. The filter cake was dried to yield 7.78 grams of the cis-2 enantiomer pair of (R,S)-(cyano)(3-phenoxyphenyl)methyl cis-3-(2,2-dichloroethenyl)-2,2-dimethylcyclopropanecarboxylate ($C_1=3.6$, $C_2=91.0$, $T_2=0.9$).

EXAMPLES 8

Preparation of a Mixture Enriched in the Trans-2 Enantiomer Pair of Cyfluthrin A slurry of 5.0 grams (0.012 mole) of solid (R,S)-(cyano)4-fluoro-3-phenoxyphenyl) trans-3-(2,2-dichloroethenyl)-2,2-dimethylcyclopropanecarboxylate ($T_1=71.0$, $T_2=28.0$), 0.5 gram (0.0036 mole) of potassium carbonate, and 0.05 gram (0.00012 mole) of tricaprylmethylammonium chloride in 10.0 grams of n-heptane was stirred at room temperature for approximately 17 hours. The basic mixture was neutralized with dilute hydrochloric acid and stirred for approximately 30 minutes. This mixture was filtered, and the filter cake was dried to yield 4.82 grams of the trans-2-enantiomeric pair of (R,S)-(cyano)-(4-fluoro-3-phenoxyphenyl)-methyl trans-3-(2,2-dichloroethenyl)-2,2-dimethylcyclopropanecarboxylate ($T_1=4.6$, $T_2=94.0$).

EXAMPLE 9

Preparation of a Mixture Enriched in the IR,cis S Bromo Analog of Isomer I of Cypermethrin from a Mixture of Diastereomers A solution of 9.4 grams (0.019 mole) of (R,S)-(cyano)(3-phenoxyphenyl)methyl 1R,cis-3-(2,2-dibromoethenyl)-2,2-dimethylcyclopropanecarboxylate (1R,cis S=46.0%, 1R,cis R=52.0%) in 18 grams of n-heptane was stirred at room temperature until a slurry formed. To this slurry was added 0.2 gram (0.00076 mole) of 18-crown-6 and 1.0 gram (0.0072 mole) of potassium carbonate. This mixture was stirred at room temperature for approximately 20 hours. A sample of the solid was submitted to gas chromatographic analysis (area %) was found to contain 87.8% (S)-(cyano)(3-phenoxyphenyl)-methyl 1R,cis-3-(2,2-dibromoethenyl)-2,2-dimethylcyclopropanecarboxylate and 6.9% of the 1R,cis R isomer.

EXAMPLE 10

Preparation of the Cis-2 Enantiomer Pair of (R,S)-(cyano)(3-phenoxyphenyl)methyl Cis-3-(2,2-dichloroethenyl)-2,2-Dimethylcyclopropanecarboxylate Using Potassium Fluoride and Tricaprylmethylammonium Chloride A slurry of 10.0 grams (0.024 mole) of (R,S)-(cyano)(3-phenoxyphenyl)methyl cis-3-(2,2-dichloroethenyl)-2,2-dimethylcyclopropanecarboxylate ($C_1=53.9$, $C_2=44.4$, $T_1$ and $T_2=1.7$), 0.1 gram (0.00025 mole) of tricaprylmethylammonium chloride, and 1.0 gram (0.02 mole) of potassium fluoride in 20 grams of n-heptane was stirred at room temperature for two hours. The reaction mixture was neutralized with dilute hydrochloric acid and was stirred for approximately 30 minutes. This mixture was filtered, and the filter cake was dried to yield 8.84 grams of the cis-2 enantiomer pair of (R,S)-(cyano)(3-phenoxyphenyl)methyl cis-3-(2,2-dichloroethenyl)-2,2-dimethylcyclopropanecarboxylate ($C_1=7.0$, $C_2=90.0$).

EXAMPLES 11–50

The appended tables illustrate other conditions effective for practice of the invention. Table 1 summarizes conditions and results for a process conducted substantially as described in Example 1 with the variations as indicated. Tables 2 and 3 have the same relationship to Examples 3 and 4, respectively. "Benzoin" in the tables means the benzoin by-product described above in this specification. "NR" means not reported.

TABLE 1

Preparation of Mixtures Enriched in Cis-2 Enantiomer Pair of Cypermethrin

| Exp. No. | Catalyst[a] Type | Catalyst[a] (g) | Solvent Type[b] | Base Type[c] | Reaction Time (Hr) | Starting Material Analysis[d] | Amt (g) | Product Analysis (Area % HPLC) $C_1$ | $C_2$ | Trans Total | Benzoin Total |
|---|---|---|---|---|---|---|---|---|---|---|---|
| 11 | A | 0.1 | A | A | 2.0 | A | e | 17.8 | 80.0 | 2.3 | NR |
|  |  |  |  |  | 4.0 |  | e | 9.8 | 87.6 | 2.6 | NR |
|  |  |  |  |  | 6.0 |  | e | 7.3 | 90.4 | 2.3 | NR |
|  |  |  |  |  | 8.0 |  | 8.9 | 6.7 | 92.3 | NR | NR |
| 12 | A | 0.1 | A | B | 18.0 | B | 8.7 | 6.2 | 92.6 | 0.5 | NR |
| 13 | A | 0.1 | B | C | 18.0 | B | 8.9 | 5.8 | 92.2 | 0.5 | NR |
| 14 | A | 0.2 | C | D | 17.5 | C | 7.7 | 3.0 | 86.0 | 1.2 | 1.2 |
| 15 | A | 0.2 | A | E | 17.0 | C | 8.5 | 4.0 | 93.5 | 2.0 | NR |
| 15 | See Base |  | A | F | 5.5 | C | — | 26.0 | 71.0 | NR | NR |
|  |  |  |  |  | 11.0 |  | — | 22.0 | 75.0 | NR | 1.3 |
|  |  |  |  |  | 23.0 |  | 8.4 | 5.0 | 92.0 | NR | 2.6 |
| 17 | A | 0.2 | A | G | 18.0 | C | 9.1 | 7.1 | 89.2 | NR | 2.5 |
| 18 | A | 0.2 | A | H | 17.5 | C | 8.1 | 5.0 | 92.0 | 0.8 | NR |
| 19 | B | 0.5 | A | C | 18.0 | D | 8.4 | 6.0 | 93.7 | NR | 0.2 |
| 20 | B | 0.5 | A | A | 18.0 | D | 8.9 | 6.6 | 92.4 | NR | 0.3 |
| 21 | B | 0.5 | A | I | 18.0 | D | 8.4 | 19.0 | 80.5 | NR | NR |
| 22 | B | 0.5 | A | J | 18.0 | D | 8.9 | 5.8 | 93.6 | NR | NR |
| 23 | C | 0.5 | A | C | 18.0 | D | 8.1 | 22.0 | 77.0 | NR | NR |
| 24 | C | 0.5 | A | A | 18.0 | D | 8.5 | 18.0 | 80.0 | NR | NR |
| 25 | C | 0.5 | A | K | 20.0 | D | 8.0 | 7.0 | 89.0 | NR | 2.0 |
| 26 | D | 0.4 | A | L | 8.0 | D | 9.9 | 19.8 | 71.8 | 0.6 | NR |
| 27 | E | 0.2 | A | L | 24.0 | C | 7.8 | 5.0 | 92.6 | 1.4 | NR |
| 28 | F | 0.4 | A | L | 19.0 | C | 8.3 | 4.0 | 79.0 | NR | NR |
| 29 | D | 0.2 | D | M | 22.0 | E | NR | 8.8 | 86.0 | 2.0 | 2.2 |
| 30 | D | 0.2 | D | N | 4.0 | E | NR | 11.6 | 82.0 | 2.2 | 3.1 |
| 31 | D | 0.2 | D | V | 22.0 | E | NR | 9.3 | 8.20 | 2.1 | 4.8 |
| 32 | D | 0.4 | A | O | 21.0 | F | NR | 8.6 | 88.0 | 2.1 | 0.1 |
| 33 | D | 0.1 | D | P | 7.0 | E | NR | 10.4 | 83.8 | 2.5 | 2.3 |
| 34 | D | 0.2 | D | Q | 18.0 | E | NR | 9.0 | 86.0 | 2.0 | 2.0 |
| 35 | D | 0.2 | D | R | 18.0 | E | NR | 10.0 | 84.0 | 2.0 | 2.3 |
| 36 | E | 0.28 | D | P | 18.0 | E | NR | 9.8 | 86.0 | 1.9 | 1.1 |
| 37 | D | 0.2 | D | S | 17.0 | E | NR | 17.0 | 80.0 | 2.0 | NR |
| 38 | G | 0.2 | D | P | 18.0 | E | NR | 9.0 | 88.0 | 2.0 | NR |
| 39 | G | 0.2 | D | T | 46.0 | E | NR | 8.2 | 87.0 | 2.0 | NR |
| 40 | D | 0.2 | D | T | 24.0 | E | NR | 7.7 | 89.0 | 2.1 | 0.1 |
| 41 | D | 0.2 | D | U | 26.0 | E | NR | 9.0 | 85.0 | 2.1 | 3.0 |
| 42 | D | 0.2 | D | W | 18.0 | E | NR | 10.8 | 86.0 | 2.4 | 0.5 |
| 43 | D | 0.2 | D | X | 18.0 | E | NR | 9.0 | 86.0 | 1.7 | 1.8 |

[a]Catalyst
A = Tricaprylmethylammonium chloride
B = 18-crown-6
C = Tris(3,6-dioxaheptyl)amine
D = Tetrabutylammonium chloride/acetonitrile (50/50 mixture)
E = Tetrabutylammonium chloride
F = Tetrabutylammonium chloride/methanol (50/50 mixture)
G = Tetraethylammonium chloride/acetonitrile (50/50 mixture)
[b]Solvent
A = n-heptane (20 grams)
B = n-octane (20 grams)
C = n-pentane (20 grams)
D = n-heptane (10 grams)
[c]Base (1.0 gram except as indicated)
A = Solid potassium cyanide
B = Solid calcium hydroxide
C = Solid potassium carbonate
D = Aqueous, 10% sodium carbonate solution (10 ml)

TABLE 1-continued

E = Aqueous, 10% sodium carbonate/sodium bicarbonate - pH 9.5 (10 ml)
F = Catalyst/base compound: tricaprylmethylammonium phenolate (0.1 g)
G = Solid sodium cyanide
H = Borate buffer solution - pH 10 (VWR scientific) (10 ml)
I = Potassium acetate
J = Potassium cyanate
K = Potassium phenoxide
L = Solid sodium carbonate
M = Solid sodium acetate (0.5 gram)
N = Solid potassium cyanate (0.5 gram)
O = Potassium cyanide (2.2 grams)/sodium metabisulfite (1.0 gram)
P = Solid sodium cyanide (0.5 gram)
Q = Sodium cyanide (0.5 gram)/sodium sulfite (0.5 gram)
R = Sodium cyanide (0.5 gram)/sodium bicarbonate (0.5 gram)
S = Sodium cyanide (0.5 gram)/sodium hydrogen sulfite (0.5 gram)
T = Sodium cyanide (0.5 gram)/sodium metabisulfite (0.5 gram)
U = 3-(2,2-Dichloroethenyl)-2,2-dimethylcyclopropanecarboxylic acid, potassium salt (0.5 gram)
V = Solid potassium acetate (0.5 gram)
W = Sodium cyanide (0.5 gram)/sodium hydrosulfite (0.5 gram)
X = Sodium cyanide (0.5 gram)/sodium sulfate (0.5 gram)
$^d$Starting Material Analysis - area % HPLC (10.0 g starting material in Exp. 11-28, 5.0 g in Exp. 29-43)
A. $C_1 = 54.1$; $C_2 = 44.2$; $T_1 + T_2 = 1.7$
B. $C_1 = 52.9$; $C_2 = 45.1$; $T_1 + T_2 = 2.0$
C. $C_1 = 53.8$; $C_2 = 42.0$; $T_1 + T_2 = 4.0$
D. $C_1 = 51.7$; $C_2 = 46.8$; $T_1 + T_2 = 1.5$
E. $C_1 = 51.9$; $C_2 = 47.1$; $T_1 + T_2 = 2.0$
F. Same as E but 10 g starting material used
$^e$Gas chromatographic analysis (area %) rather than HPLC.

TABLE 2

Preparation of Mixtures Enriched in Cis-2 and Trans-2 Enantiomer Pairs of Cypermethrin

| Exp. No. | Catalyst$^a$ (g) | Solvent$^b$ Type | Solvent$^b$ (g) | Base$^c$ | Reaction Time (Hr) | Starting Material Analysis$^d$ | AMT (g) | Product Analysis (Area % HPLC Normalized) $C_1$ | $C_2$ | $T_1$ | $T_2$ | Total Benzoin |
|---|---|---|---|---|---|---|---|---|---|---|---|---|
| 44 | 0.2 | A | 5 | A | 40 | A | NR | 17.4 | 27.9 | 12.0 | 27.6 | 15.1 |
| 45 | 0.2 | B | 20 | A | 17 | A | NR | 15.4 | 26.6 | 13.1 | 28.3 | 16.6 |
| 46 | 0.4 | C | 20 | B | 72 | B | 9.64 | 5.0 | 41.0 | 3.0 | 47.7 | 1.5 |
| 47 | 0.4 | C | 20 | C | 18 | B | NR | 5.8 | 41.0 | 3.8 | 47.6 | 0.5 |

$^a$Catalyst:
Tricaprylmethylammonium chloride (Exp. No. 44, 45)
Tetrabutylammonium chloride/acetonitrile, 50/50 (Exp. No. 46, 47)
$^b$Solvents
A = n-Pentane
B = 19.0 g of n-pentane and 1.0 g of methanol
C = n-heptane
$^c$Base:
A = Aqueous, 10% sodium carbonate solution (10 ml) - 1.0 g
B = Potassium cyanide (1.0 g)/sodium metabisulfite (1.0 g)
C = Potassium cyanide (1.0 g)/potassium metabisulfite (1.2 g)
$^d$Analysis (area % by HPLC) 10.0 g of starting material used in Ex. 45, 12.6 g in Ex. 44; 10.0 g in Ex. 46 and 47
Ex. 44 and 45
A = $C_1 = 26.7$; $C_2 = 18.9$; $T_1 = 23.0$; $T_2 = 16.0$; Total Benzoins = 0.6
Ex. 46 and 47
B = $C_1 = 26.6$; $C_2 = 22.7$; $T_1 = 27.6$; $T_2 = 20.7$

TABLE 3

Preparation of Mixtures Enriched in Trans-2 Enantiomer Pair of Cypermethrin

| Exp. No. | Catalyst$^a$ (g) | Solvent$^b$ (g) | Base Type$^e$ | Base (g) | Reaction Time (Hr) | Starting Material Analysis$^d$ | AMT (g) | Total cis | $T_1$ | $T_2$ | Total Benzoin |
|---|---|---|---|---|---|---|---|---|---|---|---|
| 48 | 0.4 | 40 | A | 1.0 | 18 | A | 18.3 | NR | 7.1 | 90.1 | 1.4 |
| 49 | 1.0 | 200 | B | 10 | 13 | B | 89.2 | NR | 9.0 | 91.0 | NR |
| 50 | 1.0 | 200 | B | 10 | 13 | B | 94.5 | NR | 2.9 | 96.3 | NR |

$^a$Catalyst: Tricaprylmethylammonium chloride
$^b$Solvent: n-heptane
$^c$Base:
A = Aqueous solution of sodium carbonate and sodium bicarbonate; pH 9.0-9.5; 10 ml.
B = Solid sodium carbonate
$^d$Starting material analysis
A = 20.0 grams; total cis = NR; $T_1 = 56.1$; $T_2 = 41.0$
B = 100.0 grams; total cis = 1.1; $T_1 = 55.4$; $T_2 = 43.5$

I claim

1. A process for converting less pesticidally active isomers in a starting mixture of isomers of a crystallizable pyrethroid, having an asymmetric carbon to which an epimerizable proton is attached, to more pesticidally active isomers, which comprises:

(a) forming a slurry of the starting mixture in a liquid medium consisting essentially of an aliphatic or alicyclic hydrocarbon of 5 to 16 carbons in which the more pesticidally active isomers are substantially insoluble, the ratio of starting mixture to hydrocarbon by weight being about 1:1 to 1:4, (b) contacting the slurry with a base and a catalyst, said catalyst being substantially soluble in the liquid medium and selected from a quaternary ammonium compound, a quaternary phosphonium compound, and a crown either, the ratio of starting material to base by weight being from about 10:1 to 20:1 and the ratio of starting material to catalyst by weight being from about 10:1 to 100:1, (c) agitating the resulting mixture while maintaining a temperature in the range of 5 to 35° C., for a period of from about 2 to about 24 hours, and (d) separating the resulting crystallized isomers from the liquid medium.

2. The process of claim 1 wherein the starting mixture comprises the more active and less active enantiomers of cypermethrin and the resulting crystalline product predominately comprises the more active enantiomers.

3. The process of claim 2 wherein the starting mixture comprises the four enantiomer pairs of cypermethrin and the resulting crystalline product predominately comprises the cis-2 and trans-2 enantiomer pairs.

4. The process of claim 2 wherein the starting mixture comprises the cis-1 and cis-2 enantiomer pairs of cypermethrin and the resulting crystalline product predominately comprises the cis-2 enantiomer pair.

5. The process of claim 2 wherein the starting mixture comprises the trans-1 and trans-2 enantiomer pairs of cypermethrin and the resulting crystalline product predominately comprises the trans-2 enantiomer pair.

6. The process of claim 1 wherein the starting mixture comprises the more active and less active enantiomers of cyfluthrin and the resulting crystalline product predominately comprises the more active enantiomers.

7. The process of claim 6 wherein the starting mixture comprises the four enantiomer pairs of cyfluthrin and the resulting crystalline product predominately comprises the cis-2 and trans-2 enantiomer pairs.

8. The process of claim 6 wherein the starting mixture comprises the cis-1 and cis-2 enantiomer pairs of cyfluthrin and the resulting crystalline product predominately comprises the cis-2 enantiomer pair.

9. The process of claim 6 wherein the starting mixture comprises the trans-1 and trans-2 enantiomer pairs of cyfluthrin and the resulting crystalline product predominately comprises the trans-2 enantiomer pair.

10. The process of claim 1 wherein the starting mixture comprises the more active and less active enantiomers of (cyano)(3-phenoxyphenyl)methyl 3-(2,2-dibromoethenyl)-2,2-dimethylcyclopropanecarboxylate and the resulting crystalline product predominately comprises the more active enantiomers.

11. The process of claim 10 wherein the starting mixture comprises the 1R,cis S and 1R,cis R isomers of (cyano)(3-phenoxyphenyl)methyl 3-(2,2-dibromoethenyl)-2,2-dimethylcyclopropanecarboxylate and the resulting product predominately comprises the 1R,cis S isomer.

12. The process of claim 1 wherein the base is a basic salt of an organic or inorganic acid.

13. The process of claim 12 wherein the base is an aqueous solution of a basic salt of an organic or inorganic acid.

14. The process of claim 12 wherein the base is a solid.

15. The process of claim 1 wherein the slurry is substantially anhydrous.

16. The process of claim 1 wherein the base is a solid alkali or alkaline earth metal oxide, hydroxide, carbonate, bicarbonate, cyanide, cyanate, acetate or borate, an aqueous solution of one or more thereof, or a trialkyl amine.

17. The process of claim 1 wherein an adduct of the base and catalyst are formed prior to contact with the slurry in step (b).

18. The process of claim 1 wherein the starting mixture comprises the cis-1 and cis-2 enantiomer pairs of cypermethrin, the liquid medium is at least one aliphatic or cycloaliphatic hydrocarbon of 5-16 carbon atoms, the base is a basic salt of an organic or inorganic acid, and the catalyst is tricaprylmethylammonium chloride.

19. The process of claim 18 wherein the liquid medium is heptane and the basic salt is an alkali metal carbonate and cyanide.

20. The process of claim 1 wherein the slurry is formed by seeding a solution of the starting mixture with at least one crystal of the more pesticidally active isomers.

21. The process of claim 1 wherein the starting mixture comprises the four enantiomer pairs of cypermethrin, the liquid medium is at least one aliphatic or cycloaliphatic hydrocarbon of 5-16 carbon atoms, the base is a basic salt of an organic or inorganic acid, and the catalyst is tricaprylmethylammonium chloride.

22. The process of claim 21 wherein the liquid medium is heptane and the basic salt is an alkali metal carbonate and cyanide.

23. The process of claim 1 wherein the starting mixture comprises the trans-1 and trans-2 enantiomer pairs of cypermethrin, the liquid medium is at least one aliphatic or cycloaliphatic hydrocarbon of 5-16 carbon atoms, the base is a basic salt of an organic or inorganic acid, and the catalyst is tricaprylmethylammonium chloride.

24. The process of claim 23 wherein the liquid medium is heptane and the basic salt is an alkali metal carbonate and cyanide.

25. The process of claim 1 wherein the starting mixture comprises the four enantiomer pairs of cypermethrin or cyfluthrin wherein the amounts of the cis-2 and trans-2 enantiomer pairs each range from about 15 to 25 wt. % and the crystalline product comprises at least about 30 wt. % of each of the cis-2 and trans-2 enantiomer pairs.

26. The process of claim 1 wherein the starting mixture comprises about 20-80 wt. % of the cis-1 and about 80-20 wt. % of the cis-2 enantiomer pairs of cypermethrin or cyfluthrin and the crystalline product comprises at least 30-90 wt. % of the cis-2 pair.

27. The process of claim 1 wherein the starting mixture comprises a mixture of about 20-80 wt. % of the trans-1 and about 80-20 wt. % of the trans-2 enantiomers of cypermethrin or cyfluthrin and the crystalline product comprises at least 30-90 wt. % of the trans-2 pair.

28. The process of claim 1 wherein, in step (b), the slurry containing base and catalyst is contacted with a scavenger for aldehydes.

29. The process of claim 28 wherein the scavenger for aldehydes is an alkali metal metabisulfite, hydrogen sulfite or hydrosulfite.

30. The process of claim 28 wherein the base is an alkali metal cyanide and the catalyst is a tetraalkyl-($C_1$–$C_5$)ammonium halide dissolved in an aprotic organic solvent.

31. The process of claim 28 wherein the base is potassium cyanide, the catalyst is a tetraalkyl ($C_1$–$C_5$) ammonium halide dissolved in an organic nitrile, and the scavenger for aldehydes is an alkali metal metabisulfite.

* * * * *